United States Patent [19]

Grollier

[11] Patent Number: 4,801,302
[45] Date of Patent: Jan. 31, 1989

[54] PROCESS FOR DYEING HUMAN HAIR WITH BRAZILIN OR ITS HYDROXYL DERIVATIVE AND COMPOSITIONS EMPLOYED

[75] Inventor: Jean F. Grollier, Paris, France
[73] Assignee: L'Oreal, Paris, France
[21] Appl. No.: 46,657
[22] Filed: May 5, 1987
[30] Foreign Application Priority Data
  May 7, 1986 [LU] Luxembourg ............... 86422
[51] Int. Cl.[4] ................................. A61K 7/13
[52] U.S. Cl. ........................... 8/429; 8/405; 8/425; 8/624
[58] Field of Search .............. 8/425, 429, 624, 405
[56] References Cited

U.S. PATENT DOCUMENTS 2,338,745  1/1944  Riper et al. ............... 167/88
3,215,605  11/1965  Soloway .................. 8/425
4,358,286  11/1982  Grollier et al. ............. 8/425

FOREIGN PATENT DOCUMENTS 2028818  12/1970  Fed. Rep. of Germany .
 383920   3/1908  France .
1324005   3/1963  France .
1363266   5/1964  France .
0124393  11/1984  France .
0133129   2/1985  France .
 470356   8/1937  United Kingdom .
2132642   7/1984  United Kingdom .

OTHER PUBLICATIONS

*Fairchild's Dictionary of Textiles,* Fairchild Pub., N.Y., 1962, p. 381.
Colour Index, 3rd Rd., Society of Dyers and Colourists, 1971, vol. 3, pp. 3239 & 3251-3252.
Kirk-Othmer Encyclopedia of Chemical Technology, 3rd Ed., Wiley-Interscience, vol. 8 (1979) p. 360.
H. S. Redgrove & G. A. Fern, "Hair-Dyes and Hair-Dyeing Chemistry and Technique," 3rd Edition (Heinemann, 1939) pp. 59-64.

*Primary Examiner*—Paul Lieberman
*Assistant Examiner*—Linda D. Skaling
*Attorney, Agent, or Firm*—Marshall, O'Toole, Gerstein, Murray & Bicknell

[57] ABSTRACT

Process for dyeing hair in several separate steps consisting in applying a cosmetically acceptable composition containing at least one cupric salt and, before or after this application, a cosmetically acceptable composition containing a dye chosen from brazilin and its hydroxyl derivative.

16 Claims, No Drawings

PROCESS FOR DYEING HUMAN HAIR WITH BRAZILIN OR ITS HYDROXYL DERIVATIVE AND COMPOSITIONS EMPLOYED

The invention relates to a new process enabling hair and more particularly living human hair to be dyed with natural dyes from the brazilin group, and to the compositions and the devices employed in implementing this process.

The dyeing of hair, especially living human hair with the aid of natural dyes, which has been known, especially in the case of henna, since ancient times, and has for many years been abandoned in favour of more reproducible and more easily prepared synthetic dyes, has been the subject of revived interest for a number of years.

From a technical standpoint, the main defects of what are known as natural dyes are a lack of affinity for hair fibres and more especially for living human hair, occasionally related to a lack of dye solubility, and poor light and washing resistance. These defects are to be found particularly where blue and red dyes are concerned.

Brazilin and its hydroxyl derivative, haematoxylin, are known as such and it has been found that their affinity for living human hair is limited and that they have a mediocre resistance to washing and to light.

The use of the mordanting method, consisting in employing metal derivatives such as iron and aluminium, to increase the dyeing power of natural dyes, has already been proposed in the past, especially in the textile field.

This method, while being of interest especially in the case of wool, cannot be used in practice for dyeing living hair, insofar as it generally requires high temperatures, which are incompatible with the dyeing of living hair. On this subject, reference is made to the work by S. Redgrove and G.A. Foan, entitled Hair Dyes and Hair Dyeing Chemistry and Technique (1939), pages 59 to 64.

European Patent Application No. 133,129 also describes a hair-dyeing process consisting in pretreating the keratinous fibres with a mixture of surfactants and of metals of groups II to V of the Periodic Classification, and more particularly aluminium, at acidic pH. This process is applicable to many natural dyes including haematoxylin, brazilin, lawsone, camomile extract, and the like.

Strong and deep shades cannot, however, be obtained with this process.

The applicant has found that it was possible to produce a strong colour exhibiting improved resistance to washing and to light, by combining the dye with brazilin or its hydroxyl derivative with a pre- or posttreatment with cupric salts.

The subject of the invention is therefore a process for dyeing human hair and especially living human hair, comprising several steps one of which consists in applying a solution of cupric salt to the hair and, before or after this treatment, applying the solution containing brazilin or its hydroxyl derivative.

Another subject of the invention is a dyeing device or kit with several compartments enabling the process to be implemented.

Other subjects of the invention will become apparent from reading the description and the examples which follow.

The process for dyeing hair and especially living human hair according to the invention is essentially characterized by the application, in separate steps, of at least one composition comprising at least one cupric salt in a cosmetically acceptable medium and, before or after this application, a composition containing, in a cosmetically acceptable medium, at least one dye corresponding to the formula:

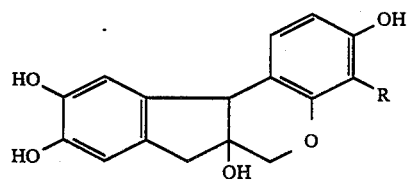

in which R denotes H or OH.

The dye corresponding to the formula (I) may be employed in accordance with the invention in the form of pure product, in the form of a plant extract produced from natural products containing it, and more particularly from sapanwood, from brazilwood, from red wood or pernambuco wood in the case of brazilin and from logwood or bluewood in the case of haematoxylin, in accordance with traditional extraction methods which are known per se or alternatively in the form of logwood or brazilwood powders in which the main dyes are haematoxylin and brazilin respectively.

The dyes according to the invention are employed in concentrations of active substance of brazilin or haematoxylin of between 0.05 and 5% and more particularly between 0.2 and 2%.

The cupric salts which may be employed in accordance with the invention are the salts which are acceptable from a cosmetic standpoint, preferably chloride, sulphate, nitrate, acetate, lactate and glycinnate, sulphonate, and still more particularly chloride, sulphate, nitrate and acetate.

The copper content of the composition containing the cupric salt is between 0.01 and 2% by weight based on the total weight of the composition, and more particularly between 0.1 and 1% and still more particularly between 0.1 and 0.5%.

The compositions employed in accordance with the invention are generally aqueous compositions which may contain ingredients usually employed in cosmetic compositions intended for dyeing hair, such as solvents, surface-active agents, thickeners, conditioning agents, alkalifying or acidifying agents for adjusting the pH, preserving agents, perfumes, and the like.

The composition containing the cupric salt is preferably in the form of a solution which has a pH of between 3 and 11.

The composition containing brazilin or its hydroxyl derivative is preferably in the form of a more or less thickened solution or emulsion, for example a cream, gel or aerosol foam, and it has a pH of between 3 and 11. This composition containing brazilin or its hydroxyl derivative may also be in the form of an anhydrous solution or powder which are diluted with water or an aqueous carrier at the time of use, the pH of the diluted composition being between 3 and 11.

The agents employed for adjusting the pH are chosen more particularly, in the case of alkalifying agents, from alkanolamines such as monoethanolamine, triethanolamine, alkali metal or ammonium hydroxides and carbonates, aqueous ammonia, aliphatic or aromatic amines such as morpholine, diethylamine and hydroxylamine. Aqueous ammonia, aliphatic or aromatic amines or alkanolamines are preferably employed with the cupric solution. The acidifying agents are organic or inorganic acids, such as lactic acid, acetic acid, tartaric acid, phosphoric acid, hydrochloric acid and citric acid.

The solvents which can be employed in these compositions are organic solvents which are acceptable from a cosmetic standpoint, and more particularly alcohols such as ethyl alcohol, isopropyl alcohol, benzyl alcohol, phenylethyl alcohol, or glycols or glycol ethers such as, for example, ethylene glycol and its monomethyl, monoethyl and monobutyl ethers, propylene glycol, butylene glycol, dipropylene glycol, and alkyl ethers such as diethylene glycol monobutyl ether, in concentrations of between 0.5 and 75% and, preferably, between 2 and 50% by weight based on the total weight of each of the compositions.

The surface-active agents which can be employed are anionic, cationic, nonionic or amphoteric surface-active agents or a mixture thereof. These surface-active agents are preferably employed in proportions of between 0.1 and 50% by weight, and advantageously between 1 and 20% by weight based on the total weight of the composition. Among the surface-active agents there may be mentioned anionic agents such as, in particular, the alkali metal salts, the magnesium salts, the ammonium salts, the amine salts and the alkanolamine salts of the following compounds:

alkyl sulphates, alkyl ether sulphates, alkylamidosulphates ethoxylated or otherwise, alkylamidosulphonates, alpha-olefinsulphonates, and alkylsulphoacetates; the alkyl radicals in these compounds having a linear chain with 12 to 18 carbon atoms. It is also possible to employ the abovementioned salts of fatty acids such as lauric, myristic, oleic, ricinoleic, palmitic or stearic acids, of hydrogenated copra oil acids, and of carboxylic acids of polyglycol ethers.

As cationic surface-active agents there may be employed, in particular, fatty amine salts and quaternary ammonium salts such as alkyldimethylbenzylammonium or dimethyldialkylammonium chlorides and bromides, alkylpyridinium salts, and imidazoline derivatives. The alkyl groups in the abovementioned quaternary ammonium derivatives are groups containing a long chain which preferably has between 12 and 18 carbon atoms. Amine oxides may also be mentioned among these compounds of cationic nature.

The amphoteric surface-active agents which can be employed are in particular alkylamino(mono- and di-)propionates, betaines such as alkylbetaines, N-alkylsulphotetaines and N-alkylaminobetaines, in which the alkyl radical has between 8 and 22 carbon atoms, and cycloimidinium compounds such as alkylimidazolines.

The nnonionic surface-active agents which can be used in the compositions employed in accordance with the invention may be chosen more particularly from:

(a) the products of condensation of a mono alcohol, of an α-diol, of an alkylphenol or of an amide with glycidol or a glycidol precursor corresponding, in particular, to the formula:

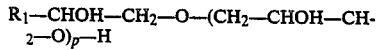

in which $R_1$ denotes an aliphatic, alicyclic or arylaliphatic radical preferably containing between 7 and 21 carbon atoms and mixtures thereof, it being possible for the aliphatic chains to contain ether, thioether or hydroxymethylene groups and p has a value of between 1 and 10 inclusive. Compounds which are particularly preferred are those in which $R_1$ denotes a mixture of alkyl radicals containing between 9 and 12 carbon atoms and p has a statistical value of 3.5 or else those in which $R_1$ denotes a $C_{10}$ alkyl radical and p has a statistical value of 2.5. Compounds of this kind are described in particular in French Pat. No. 2,091,516.

(b) Compounds corresponding to the formula:

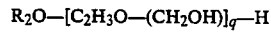

in which $R_2$ denotes an alkyl, alkenyl or alkylaryl radical and q is a statistical value of between 1 and 10. The preferred compounds are those in which $R_2$ denotes a $C_{12}H_{25}$ group and q has a statistical value from 4 to 5. These compounds are described in particular in French Pat. No. 1,477,048.

(c) Compounds corresponding to the formula:

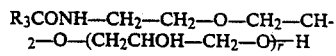

in which $R_3$ denotes a radial or a mixture of straight-chain or branched, saturated or unsaturated aliphatic radicals which may optionally contain one or more hydroxyl groups and which have between 8 and 30 carbon atoms, of natural or synthetic origin, and r denotes an integer or decimal from 1 to 5 and represents the average degree of condensation. The compounds which are particularly preferred are those in which $R_3$ denotes a mixture of radicals derived from lauric, myristic, oleic or copra acids and r has a statistical value from 3 to 4. Compounds of this kind are described more particularly in French Pat. No. 2,328,763.

(d) Polyethoxylated or polyglycerolated alcohols, alkylphenols or fatty acids containing a $C_8$ to $C_{18}$ linear fatty chain, condensates of ethylene and propylene oxides with fatty alcohols; polyethoxylated fatty amides containing at least 5 moles of ethylene oxide; and polyethoxylated fatty amines.

The compositions employed in accordance with the invention may also contain fatty acids or their amides, such as mono- and diethanolamides of fatty acids derived from copra, of lauric acid or of oleic acid, in concentrations of between 0.05 and 10% by weight based on the total weight of the composition.

The thickening agents which may be added to the compositions employed according to the invention are preferably chosen from sodium alginate, gum arabic, xanthane gum, guar gum, cellulose derivatives such as methyl cellulose, hydroxyethyl cellulose, hydroxypropyl methyl cellulose, the sodium salt of carboxymethyl cellulose and crosslinked acrylic acid polymers.

It is also possible to use inorganic thickening agents such as bentonite.

These thickeners are employed by themselves or mixed and are preferably present in proportions of between 0.1 and 5% by weight based on the total weight of each of the compositions, and advantageously between 0.5 and 3% by weight.

The dyes which may be used in the compositions employed in accordance with the invention are preferably direct dyes such as the nitro derivatives of the benzene series, anthraquinone or azo dyes and, more particularly natural dyes such as lawsone.

Another embodiment of the invention consists in preparing the composition containing the dyes of formula I in anhydrous form in the presence of organic solvents as defined above, the composition containing less than 1% of water, and in preparing, at the time of use, the aqueous composition corresponding to the definition given above.

These anhydrous compositions may additionally contain anhydrous nonionic surface-active agents, as described in French Patent Application No. 83 07,045.

The composition containing the dyes of formula I may also be packaged in the form of a mixture of powders comprising, on the one hand, the dyes of formula I or the powdered natural products containing these and, on the other hand, flours, starchy or mucilaginous substances, silicas, powdered plants, clays, or plants powdered after their active essences have been extracted. A composition of this kind is diluted with water or a solvent or a cosmetically acceptable oil, so as to produce a product which is also known as a "poultice", which has a viscosity from 0.1 to 9 Pa s. The composition containing the cupric derivative is applied to the hair preferably before the application of the poultice.

The process according to the invention is more particularly employed by applying to the hair, in a first step, the composition containing the cupric salt at a pH of between 3 and 11, for a period of 3 to 30 minutes, followed by rinsing with water and then the application of the composition containing brazilin or its hydroxyl derivative. This second composition is left in contact with the hair for a period of 3 to 30 minutes; and the latter is then rinsed, washed if desired and dried.

A particularly advantageous form of embodiment consists in presenting the compositions employed in the process in a device with several compartments, also known as a dyeing kit, and comprising in one of the compartments the composition containing the cupric salt, and in the other compartment(s) the composition containing at least brazilin or its hydroxyl derivative.

The examples which follow are intended to illustrate the invention without, however, being limiting in their nature.

EXAMPLE 1

The following compositions are prepared:

| Composition A | | |
|---|---|---|
| $CuSO_4.5H_2O$ | | 1 g |
| Monoethanolamine | q.s. pH: 9.5 | |
| Water | q.s. | 100 g |
| Composition B | | |
| Haematoxylin | | 1 g |
| 2-Butoxyethanol | | 50 g |
| Natural pH | 3.5 | |
| Water | q.s. | 100 g |

90% white hair is treated with composition A for 5 minutes. It is rinsed; composition B is applied, is left in place for 30 minutes and is rinsed off. A strong night-blue colour is obtained, which is particularly resistant to washing and to light on permanently waved hair.

EXAMPLE 2

The following compositions are prepared:

| Composition A | | |
|---|---|---|
| $CuSO_4.5H_2O$ | | 1 g |
| Monoethanolamine | q.s. pH: 9.5 | |
| Water | q.s. | 100 g |
| Composition B | | |
| Brazilin | | 1 g |
| Haematoxylin | | 0.1 g |
| Diethylene glycol monobutyl ether | | 50 g |
| Natural pH | 3.5 | |
| Water | q.s. | 100 g |

90% white hair is treated with the composition A for 5 minutes. It is rinsed and composition B is applied and left in place for 20 minutes. Rinsing and drying are carried out. A purple-violet colour is produced.

EXAMPLE 3

The following compositions are prepared:

| Composition A | | |
|---|---|---|
| Haematoxylin | | 1.5 g |
| 2-Butoxyethanol | | 50 g |
| Monoethanolamine | q.s. pH: 8.5 | |
| Water | q.s. | 100 g |
| Composition B | | |
| $CuSO_4.5H_2O$ | | 1 g |
| Natural pH 4.8 | | |
| Water | q.s. | 100 g |

Brown hair is treated with the dye composition A. After being left in place for 30 minutes this is rinsed off and the composition B is then applied and left in place for 5 minutes. After rinsing, an ashen brown colour is obtained.

EXAMPLE 4

The following compositions are prepared:

| Composition A | | |
|---|---|---|
| $CuSO_4.5H_2O$ | | 0.5 g |
| $NH_4OH$ | q.s. pH: 10.8 | |
| Sodium alkyl ether sulphate at a concentration of 0.6 meq/g | | 5 g |
| Xanthane gum sold under the trade name "Keltrol" by Kelco | | 0.32 g |
| Water | q.s. | 100 g |
| Composition B | | |
| Lawsone | | 0.5 g |
| Haematoxylin | | 0.2 g |
| Ethyl alcohol | | 5 g |
| Diethylene glycol monobutyl ether | | 45 g |
| Nonylphenol oxyethylenated with 9 moles of ethylene oxide | | 10 g |
| Natural pH 4 | | |
| Water | q.s. | 100 g |

90% white hair is treated with the composition A, which is left in place for 10 minutes. It is rinsed and the dyeing composition B is applied and left in place for 20 minutes. After rinsing, a matt ashen brown colour is obtained.

EXAMPLE 5

| Composition A | | |
|---|---|---|
| $CuCl_2$ | | 1 g |
| Tartaric acid | q.s. pH 4 | |
| Water | q.s. | 100 g |
| Composition B | | |
| Part 1 | | |
| Brazilin | | 1.70 g |

| -continued | | |
|---|---|---|
| Hydroxypropyl cellulose sold under the trade name "Klucel G" by Hercules | | 2 g |
| Ethyl alcohol | q.s. | 100 g |
| Part 2 | | |
| Triethanolamine laurylsulphate | | 5 g |
| Lauric diethanolamide | | 3 g |
| Quaternary polyvinylpyrrolidone copolymer with a molecular weight of 1,000,000 marketed at a concentration of 20% AS by General Aniline under the trade name Gafquat 755 | | 0.60 g As |
| Perfume preservative | q.s. | |
| Monoethanolamine | q.s. pH 9.3 | |
| Water | q.s. | 100 g |

These compositions are introduced into a multi-compartment device or "dyeing kit".

Parts 1 and 2 are mixed at the time of use in proportions of 3/7.

Dry, dirty, brown hair is treated with the composition A for 5 minutes. It is rinsed and composition B is then applied and left in place for 30 minutes. A water rinse is applied. A purple-violet brown colour is obtained.

EXAMPLE 6

| Composition A | | |
|---|---|---|
| $CuSO_4.5H_2O$ | | 1 g |
| Tartaric acid | q.s. pH 4.7 | |
| Water | q.s. | 100 g |
| Composition B | | |
| Haematoxylin | | 0.5 g |
| Ethyl alcohol | | 28.5 g |
| Dimethylethanolamine | | 1 g |
| Nonylphenol oxyethylenated with 9 moles of ethylene oxide | q.s. | 100 g |

At the time of use, the compositions B is diluted with water in proportions of 4/6; natural pH 8.7.

Brown hair is treated with the composition A for 5 minutes and is rinsed. The composition B is then applied, left in place for 30 minutes and is then rinsed off. An ashen dark brown colour is obtained.

EXAMPLE 7

| Composition A | | |
|---|---|---|
| $CuSO_4.5H_2O$ | | 1 g |
| Monoethanolamine | q.s. pH 9.3 | |
| Water | q.s. | 100 g |
| Composition B | | |
| Brazilin | | 2 g |
| Powdered soapwort extraction residues with a particle size of 90 μm | | 30 g |
| Corn cobs | | 50 g |
| Sodium carbonate | | 3 g |
| Soluble skimmed milk powder | q.s. | 100 g |

At the time of use the composition B is diluted with water in proportions of ½; natural pH 9.3.

Dry, dirty, brown hair is treated with the composition A for 5 minutes and then rinsed. The composition B is then applied for 30 minutes and is rinsed off with water. A purple-violet colour is obtained.

EXAMPLE 8

| Composition A | | |
|---|---|---|
| $Cu(NO_3)_2$ | | 1 g |
| Ammonium lauryl sulphate | | 2.4 g |
| Hydroxyethyl cellulose | | 1 g |
| Water | q.s. | 100 g |
| Natural pH 4.7 | | |
| Composition B | | |
| Part 1 | | |
| Haematoxylin | | 0.5 g |
| Brazilin | | 1 g |
| Hydroxypropyl cellulose sold under the trade name "Klucel G" by Hercules | | 2 g |
| Ethyl alcohol | q.s. | 100 g |
| Part 2 | | |
| Triethanolamine lauryl sulphate | | 5 g AS |
| Lauric diethanolamide | | 3 g |
| Quaternary polyvinylpyrrolidone copolymer with a molecular weight of 1,000,000, marketed at a concentration of 20% AS by General Aniline under the trade name "Gafquat 755" | | 0.6 g AS |
| Preservative, perfume | q.s. | |
| Monoethanolamine | q.s. pH 9.3 | |
| Water | q.s. | 100.0 g |

Parts 1 and 2 are mixed in proportions of ⅓. 90% white hair is treated with the composition A for 5 minutes. It is rinsed with water and the composition B is then applied and left in place for 20 minutes. It is rinsed off and a purplish-blue night-blue colour is obtained.

EXAMPLE 9

| Composition A | | |
|---|---|---|
| Cupric acetate | | 1 g |
| Monoethanolamine | q.s. pH 7 | |
| Water | q.s. | 100 g |
| Composition B | | |
| Part 1 | | |
| Haematoxylin | | 0.5 g |
| Hydroxypropyl cellulose sold under the trade name "Klucel G" by Hercules | | 2 g |
| Ethyl alcohol | q.s. | 100 g |
| Part 2 | | |
| Ammonium lauryl sulphate | | 5 g AS |
| Lauric diethanolamide | | 3 g |
| Quaternary polyvinylpyrrolidone copolymer with a molecular weight of 1,000,000, marketed at a concentration of 20% AS by General Aniline under the trade name "Gafquat 755" | | 0.6 g AS |
| Perfume preservative | q.s. | |
| Tartaric acid | q.s. pH 6 | |
| Water | q.s. | 100 g |

At the time of use parts 1 and 2 are mixed in proportions of 1/1. Dry, dirty, brown hair is treated with the composition A for 5 minutes. It is rinsed and composition B is then applied and left in place for 30 minutes. Rinsing is carried out. An ashen brown colour is obtained.

EXAMPLE 10

The following compositions are prepared:

| Composition A | | |
|---|---|---|
| $CuCl_2$ | | 0.5 g |
| Natural pH 4.9 | | |
| Water | q.s. | 100 g |
| Composition B | | |

|                                 |           |        |
| ------------------------------- | --------- | ------ |
|                                 | -continued |       |
| Brazilin                        |           | 2 g    |
| Diethylene glycol monobutyl ether |         | 25.0 g |
| Ethyl alcohol                   |           | 25.0 g |
| Monoethanolamine                | q.s. pH 8.5 |      |
| Water                           | q.s.      | 100 g  |

90% white, permanent-waved hair is treated with the composition A for 5 minutes. Rinsing is carried out. The composition B is then applied, left in place for 30 minutes and rinsed off. A strong purple-violet colour is obtained.

EXAMPLE 11

|                                 |           |        |
| ------------------------------- | --------- | ------ |
| Composition A                   |           |        |
| Brazilin                        |           | 2 g    |
| Ethyleneglycol monoethyl ether  |           | 10 g   |
| Triethanolamine                 | q.s. pH 8.5 |      |
| Water                           | q.s.      | 100 g  |
| Composition B                   |           |        |
| CuSO$_4$.5H$_2$O                |           | 0.5 g  |
| Triethanolamine                 | q.s. pH 9 |        |
| Water                           | q.s.      | 100 g  |

90% naturally white hair is treated with the dye composition A. This is left in place for 30 minutes and is rinsed off and composition B is then applied and left in place for 5 minutes. After rinsing, a purple-violet light-brown colour is obtained.

EXAMPLE 12

|                                 |           |        |
| ------------------------------- | --------- | ------ |
| Composition A                   |           |        |
| Brazilin                        |           | 1 g    |
| Ethyl alcohol                   |           | 10 g   |
| Water                           | q.s.      | 100 g  |
| Natural pH 4.2                  |           |        |
| Composition B                   |           |        |
| CuCl$_2$                        |           | 1 g    |
| C$_{12}$—C$_{18}$—alkyldimethylcarboxymethyl-ammonium hydroxide sold at a concentration of 30% AS under the trade name "Dehyton AB 30" by Henkel | | 7 g AS |
| Imidazolidinylurea derivative sold under the trade name "Germall 115" by Sutton Lass | | 0.1 g |
| Water                           | q.s.      | 100 g  |
| Natural pH 4.5                  |           |        |

90% naturally white hair is treated with the composition A. This is left in place for 30 minutes and is rinsed off and composition B is then applied and left in place for 5 minutes. After rinsing, a brown colour with red iridescence is obtained.

EXAMPLE 13

|                                 |           |        |
| ------------------------------- | --------- | ------ |
| Composition A                   |           |        |
| CuSO$_4$.5H$_2$O                |           | 0.9 g  |
| Natural pH 4                    |           |        |
| Water                           | q.s.      | 100 g  |
| Composition B                   |           |        |
| Dry aqueous extract of logwood  |           | 1 g    |
| Ethyl alcohol                   |           | 10 g   |
| Natural pH 5                    |           |        |
| Water                           |           | 100 g  |

90% white permanent-waved hair is treated with the cupric composition A.

This is left in place for 5 minutes and is rinsed off and the composition B is then applied and is left in place for 20 minutes.

After rinsing, the hair is dyed to a steely grey blue shade.

EXAMPLE 14

Example 13 is reproduced, the pH of the composition B being adjusted to a value of 9 with triethanolamine, and the hair is dyed to the same shade.

I claim:

1. Process for dyeing hair, consisting in applying to the said hair in separate steps wherein said steps are separated by rinsing at least one composition containing a cupric salt in a cosmetically acceptable medium and a composition containing at least one dye corresponding to the formula:

in which R denotes hydrogen or OH, in a cosmetically acceptable medium,
wherein the copper content in the composition containing said cupric salt is between 0.01 and 2% by weight, and
said dye is present in the composition containing it in a proportion between 0.05 and 5% by weight.

2. Process according to claim 1, wherein the composition containing the cupric salt is applied in a first step and the composition containing the dye of formula (I) is applied in a second step, after rinsing.

3. Process according to claim 1, wherein the composition containing at least the dye corresponding to the formula (I) is applied in a first step, followed, after rinsing, by the composition containing the cupric salt.

4. Process according to claim 1, wherein the composition containing the cupric salt has a pH of between 3 and 11 and the composition containing the dye of formula I has a pH of between 3 and 11.

5. Process according to claim 1, wherein the composition applied in the first step is kept in contact with the hair for a period of 3 to 30 minutes, in that its application is followed by a rinse with water and in that the composition applied in the second step is also kept for a period of 3 to 30 minutes, followed by a rinse.

6. Process according to claim 1, wherein the compositions employed are in the form of solutions, thickened solutions, emulsions, or aerosol foam.

7. Process according to claim 1, wherein the compositions employed are aqueous compositions additionally containing cosmetically acceptable ingredients chosen from solvents, surfactants, thickeners, conditioning agents, alkalifying or acidifying agents, preservatives, perfumes, or mixtures thereof.

8. Process according to claim 7, wherein said solvents are chosen from alcohols, glycols or glycol ethers, or alkyl ethers, and are present in the proportions of 0.5 to 75% by weight based on the total weight of the composition.

9. Process according to claim 7, wherein the compositions employed contain at least one anionic, cationic, nonionic or amphoteric surface-active agent or mixture thereof in proportions of 0.1 to 50% by weight based on the total weight of the composition.

10. Process according to claim 7, wherein at least one of the compositions contains fatty acids or fatty acid amides in proportions of 0.05 to 10% by weight.

11. Process according to claim 7, wherein at least one of the compositions additionally contains thickening agents in proportions of 0.1 to 5% by weight.

12. Process according to claim 7, wherein the composition containing a dye of formula I also contains one or more dyes chosen from nitro derivatives of the benzene series, anthraquinones, azo compounds and lawsone.

13. Process according to claim 1, wherein the composition containing the dye of formula I is in anhydrous form in a cosmetically acceptable solvent, this composition being mixed immediately before use with a cosmetically acceptable aqueous medium containing cosmetically acceptable ingredients selected from solvents, surfactants, thickeners, conditioners, alkalifying agents, preservatives, and perfumes.

14. Process according to claim 1, wherein the composition containing the dye of formula I is in the form of a mixture of powders comprising the dyes of formula I or the natural products reduced to powder containing them and flours, starchy or mucilaginous substances, silicas, powdered plants, clays, powdered plants after the extraction of their active principle, this composition being diluted at the time of use to produce a poultice having a viscosity of 0.1 to 9 Pa s.

15. Hair-dyeing kit having a plurality of compartments, including a first compartment containing a composition comprising a cupric salt in a cosmetically acceptable medium said first compartment containing no dye, and a second compartment containing a composition comprising at least one dye corresponding to the formula:

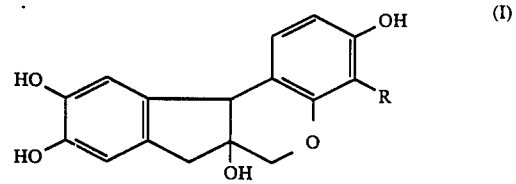

in a cosmetically acceptable medium said second compartment containing no cupric salt.

16. Hair-dyeing kit in accordance with claim 15 further including a third compartment containing a cosmetically acceptable aqueous medium comprising cosmetically acceptable ingredients selected from solvents, surfactants, thickeners, conditioning agents, alkalifying or acidifying agents, preservatives, perfumes, or mixtures thereof.

* * * * *